US010660514B2

(12) United States Patent
Ohta et al.

(10) Patent No.: US 10,660,514 B2
(45) Date of Patent: May 26, 2020

(54) IMAGE PROCESSING APPARATUS AND IMAGE PROCESSING METHOD WITH GENERATING MOTION CONTRAST IMAGE USING ITEMS OF THREE-DIMENSIONAL TOMOGRAPHIC DATA

(71) Applicant: CANON KABUSHIKI KAISHA, Tokyo (JP)

(72) Inventors: Koichi Ohta, Yokohama (JP); Yasuhisa Inao, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 96 days.

(21) Appl. No.: 15/873,059

(22) Filed: Jan. 17, 2018

(65) Prior Publication Data
US 2018/0199807 A1    Jul. 19, 2018

(30) Foreign Application Priority Data

Jan. 17, 2017   (JP) ................. 2017-005940

(51) Int. Cl.
A61B 3/00        (2006.01)
A61B 3/12        (2006.01)
A61B 3/10        (2006.01)
G06T 5/50        (2006.01)
G06T 11/60       (2006.01)
G06T 7/00        (2017.01)

(52) U.S. Cl.
CPC .......... A61B 3/0025 (2013.01); A61B 3/0058 (2013.01); A61B 3/102 (2013.01); A61B 3/1233 (2013.01); G06T 5/50 (2013.01); G06T 7/0012 (2013.01); G06T 11/60 (2013.01); G06T 2207/10101 (2013.01); G06T 2207/20216 (2013.01); G06T 2207/30041 (2013.01)

(58) Field of Classification Search
None
See application file for complete search history.

(56) References Cited

U.S. PATENT DOCUMENTS

2015/0374228 A1   12/2015   Satake et al.
2016/0371836 A1   12/2016   Kuno et al.
2018/0098812 A1*   4/2018   Ootsuki ................... A61B 3/10

FOREIGN PATENT DOCUMENTS

JP    2016-010656 A    1/2016

* cited by examiner

Primary Examiner — Idowu O Osifade
(74) Attorney, Agent, or Firm — Venable LLP

(57) ABSTRACT

An image processing apparatus that processes an image generated using at least one item of three-dimensional tomographic data out of a plurality of items of three-dimensional tomographic data obtained by conducting a plurality of optical coherence tomography scans of a subject at different times using measuring light controlled to scan a same position of the subject includes: a front image generating unit configured to generate a front image of the subject using the at least one item of three-dimensional tomographic data; a motion contrast image generating unit configured to generate a motion contrast image of the subject using the plurality of items of three-dimensional tomographic data; and a display control unit configured to display the front image on a display unit before displaying the motion contrast image.

51 Claims, 10 Drawing Sheets

IMAGE PROCESSING APPARATUS AND IMAGE PROCESSING METHOD WITH GENERATING MOTION CONTRAST IMAGE USING ITEMS OF THREE-DIMENSIONAL TOMOGRAPHIC DATA

BACKGROUND

Field

The disclosure relates to an image processing apparatus and an image processing method.

Description of the Related Art

As a method for nondestructively and noninvasively acquiring tomograms of a measuring subject such as a living body, an apparatus using optical coherence tomography (hereinafter referred to as OCT) has been put to practical use. The OCT apparatus is widely used in ophthalmologic diagnosis, in particular.

The OCT apparatus causes return light of measuring light reflected by a subject which is a measuring subject and reference light reflected by a reference mirror to interfere with each other, analyzes interference light intensity, and thereby acquires tomographic images of the measuring subject. OCT configured in this way includes time domain OCT adapted to obtain depth information on the subject by changing the position of the reference mirror and Fourier domain OCT (FD-OCT) adapted to acquire depth information on the measuring subject included in the light to be detected, by replacing the depth information with frequency information. FD-OCT (Fourier Domain Optical Coherence Tomography) includes spectral domain OCT (SD-OCT) and swept source OCT (SS-OCT). SD-OCT (Spectral Domain Optical Coherence Tomography) spectrally analyzes interference light and acquires depth information by replacing the depth information with frequency information. On the other hand, SS-OCT (Swept Source Optical Coherence Tomography) outputs light whose wavelength has been swept from a light source and acquires information.

In recent years, angiography which uses these types of OCT without using a contrast medium has been proposed. This angiographic method is called OCT angiography (hereinafter referred to as OCTA) and is capable of obtaining OCTA images by converting motion contrast data into images. Here, the motion contrast data is data obtained by taking images of the same section of a subject repeatedly and detecting time variation of the subject among the taken images and is obtained, for example, by calculating phase differences or vector differences of complex OCT signals or time variation of signal strength. After OCT image-taking is finished, calculations take a long time before OCTA images can be observed, which placed a time burden on a person to be inspected and an examiner.

Japanese Patent Application Laid-Open No. 2016-010656 discloses a technique for reducing the time required for OCTA images to be displayed. FIGS. 10A to 10C show OCTA images displayed by the technique described in Japanese Patent Application Laid-Open No. 2016-010656. The technique described in Japanese Patent Application Laid-Open No. 2016-010656 takes images of a subject multiple times while at the same time arithmetically processing data at the previous scanning position for image-taking and displays OCTA images in sequence on a line by line basis such as OCTA images 1000 to 1002 shown in FIGS. 10A to 10C.

SUMMARY

According to one aspect of the disclosure, there is provided an image processing apparatus that processes an image generated using at least one item of three-dimensional tomographic data out of a plurality of items of three-dimensional tomographic data obtained by conducting a plurality of optical coherence tomography scans of a subject at different times using measuring light controlled to scan a same position of the subject, the image processing apparatus comprising: a front image generating unit configured to generate a front image of the subject using the at least one item of three-dimensional tomographic data; a motion contrast image generating unit configured to generate a motion contrast image of the subject using the plurality of items of three-dimensional tomographic data; and a control unit configured to display the front image on a display unit before displaying the motion contrast image.

Further features of the disclosure will become apparent from the following description of exemplary embodiments with reference to the attached drawings.

DESCRIPTION OF THE EMBODIMENTS

Figure 1:
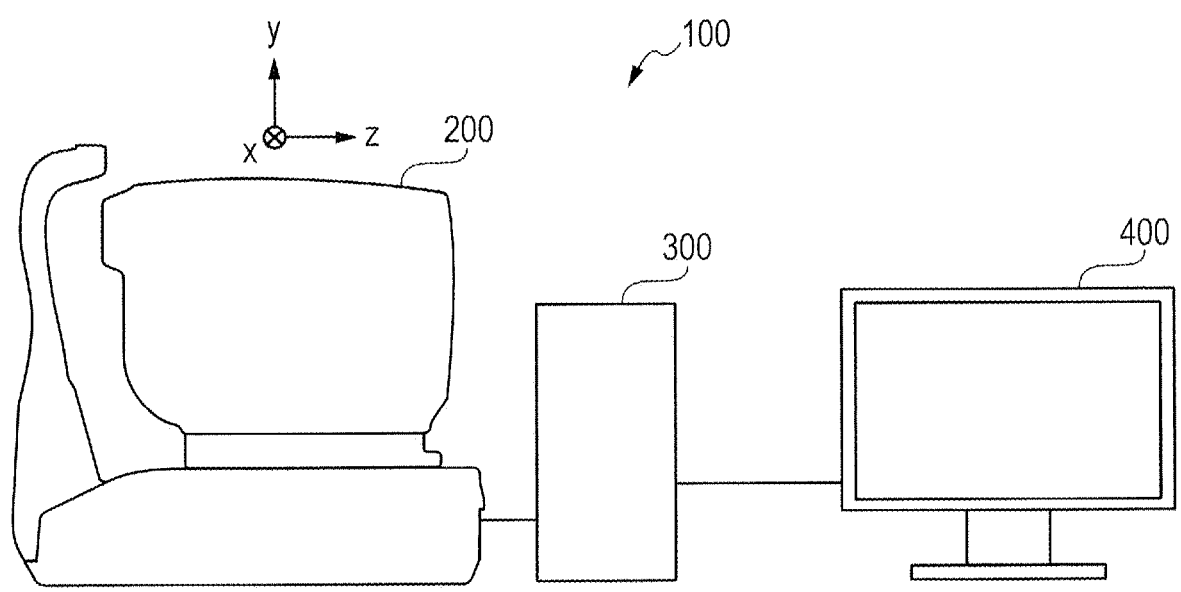
FIG. 1 shows a schematic configuration of an OCT apparatus.

Preferred embodiments of the disclosure will now be described in detail in accordance with the accompanying drawings.

In carrying out image-taking to generate an OCTA image, a person to be inspected needs to continue visual fixation for a few seconds, but there are not a few cases in which the image-taking fails because the person to be inspected blinks his/her eyes or gets out of visual fixation during image-taking and cannot continue visual fixation successfully. Conventionally, however, because the success or failure of image-taking is determined after OCTA image display, even if image-taking fails, a determination as to the need for renewed image-taking is made only after the OCTA image is displayed. Therefore, if image-taking fails, the person to be inspected will be constrained for a long time and an examiner will be late in determining the success or failure of image-taking, and consequently it will require a longer time to take an image of a single person to be inspected, making it difficult to take images of a large number of persons to be inspected. Thus, it is desired to display an image which allows success or failure to be determined as soon as possible after image-taking.

Thus, one object of an embodiment of the disclosure is to display an image based on tomographic data at an early stage after taking an image of a subject in order to determine the success or failure of the image-taking.

Therefore, an image processing apparatus according to the present embodiment processes an image generated using at least one item of three-dimensional tomographic data out of a plurality of items of three-dimensional tomographic data obtained by conducting a plurality of optical coherence tomography scans of a subject at different times using measuring light controlled to scan a same position of the subject. Also, an image processing apparatus according to the present embodiment displays a front image of a subject on a display unit before a motion contrast image of the subject is displayed, the front image of the subject being generated using at least one item of three-dimensional tomographic data and the motion contrast image being generated using a plurality of items of three-dimensional tomographic data. Alternatively, an image processing apparatus according to the present embodiment displays a front image of a subject on a display unit before generation of a motion contrast image of a subject is completed.

Consequently, the present embodiment can display an image based on tomographic data at an early stage after taking an image of a subject in order to determine the success or failure of the image-taking.

Note that, dimensions, materials, shapes, relative positions of components, and so on described in the following exemplary embodiments are not determinate, and can be changed according to the configuration and various conditions of the apparatus to which the present disclosure is applied. Also, identical or functionally similar elements are denoted by the same reference numerals in different drawings.

First Exemplary Embodiment

An OCT apparatus 100 as an optical coherence tomography apparatus according to the first exemplary embodiment of the disclosure will be described below with reference to FIGS. 1 to 7. FIG. 1 shows a schematic configuration of the OCT apparatus 100 according to the present exemplary embodiment. Note that an eye to be inspected will be described below as an example of a subject which is a measuring subject.

The OCT apparatus 100 includes an imaging optical system 200 (imaging apparatus), a control apparatus 300 (image processing apparatus) and a display unit 400. By imaging the eye to be inspected, the imaging optical system 200 acquires information about the eye to be inspected. The control apparatus 300 is connected to the imaging optical system 200 and display unit 400 in a communication-ready state, and controls the imaging optical system 200 and display unit 400. The control apparatus 300, for example, can store tomographic information about the eye to be inspected acquired by the imaging optical system 200, generate an OCTA image of the eye to be inspected from the stored tomographic information, and display the generated OCTA image on the display unit 400. The display unit 400 is connected to the control apparatus 300 and is able to display various images and information about the person to be inspected sent from the control apparatus 300.

Note that the control apparatus 300 can be configured using any general-purpose computer, but may be configured using a special-purpose computer in the OCT apparatus 100. Also, the display unit 400 can be configured using any display. Here, the imaging optical system 200, control apparatus 300 and display unit 400 are configured separately in the present exemplary embodiment, but may be configured integrally.

Figure 2:
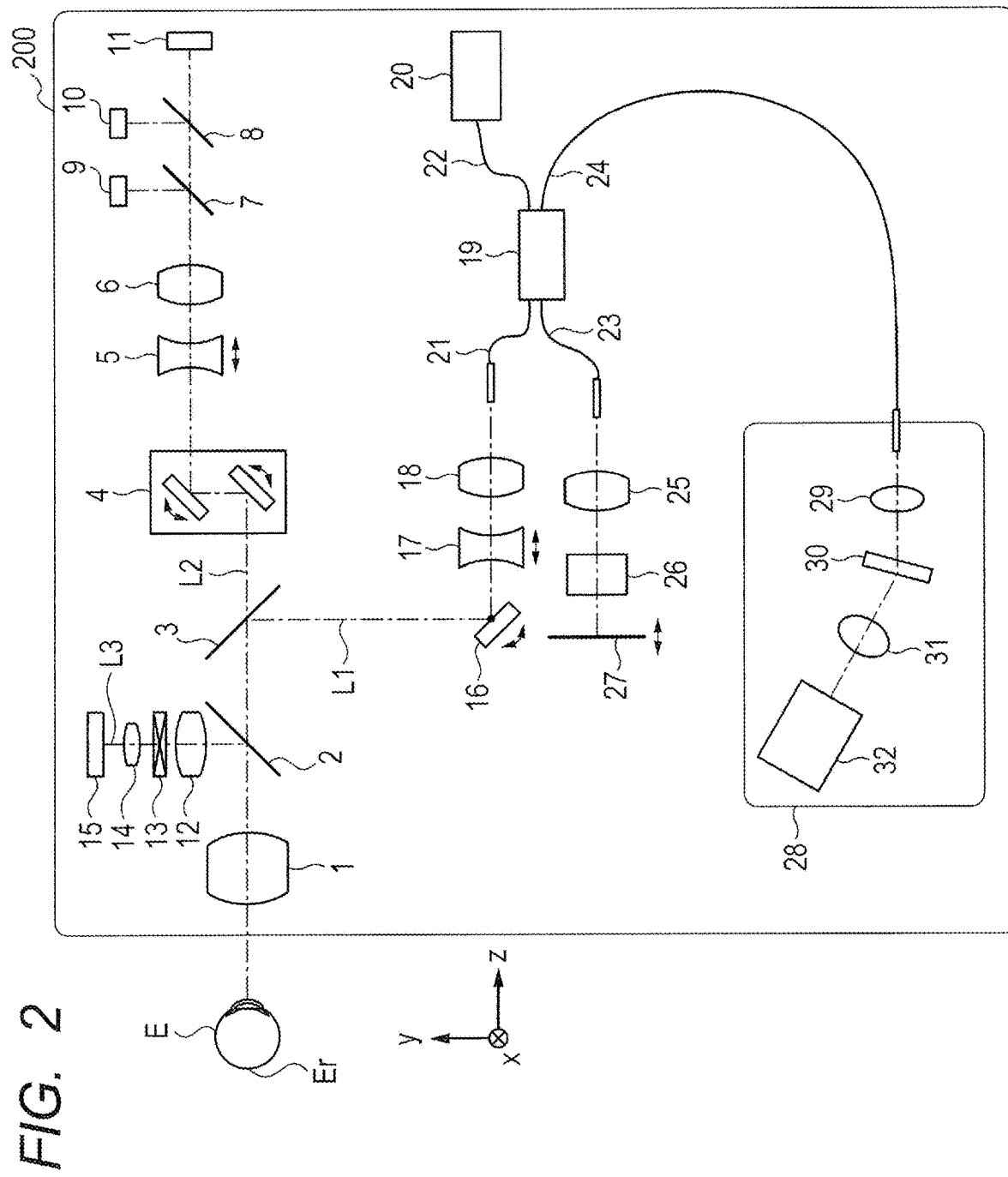
FIG. 2 shows a schematic configuration of an imaging optical system.

A configuration of the imaging optical system 200 will be described with reference to FIG. 2. FIG. 2 shows a schematic configuration of the imaging optical system 200. The imaging optical system 200 includes an objective lens 1 provided facing an eye E to be inspected, as well as a first dichroic mirror 2 and a second dichroic mirror 3 placed on an optical axis of the imaging optical system 200. An optical path from the eye E to be inspected is branched, by the dichroic mirrors, into an optical path L1 for an OCT optical system, an optical path L2 for an eye E to be inspected fundus observation system and fixation lamp, and an optical path L3 for observation of the anterior ocular segment according to the wavelength band.

According to the present exemplary embodiment, the second dichroic mirror 3 is provided in a transmission direction of the first dichroic mirror 2 and the optical path L3 for observation of the anterior ocular segment is provided in a reflection direction. Also, the optical path L2 is provided in a transmission direction of the second dichroic mirror 3 and the optical path L1 is provided in a reflection direction. However, the layout of the optical paths is not limited to the one mentioned, and the optical paths may be laid out, for example, by exchanging the transmission direction and reflection direction of the first dichroic mirror 2 as well as by exchanging the transmission direction and reflection direction of the second dichroic mirror 3. Also, although an SLO optical system is provided as a fundus observation system in the present exemplary embodiment, the fundus observation system is not limited to this, and may be configured using, for example, a fundus camera or the like.

An SLO scanning unit 4, lenses 5 and 6, a mirror 7, a third dichroic mirror 8, a photodiode 9, an SLO light source 10 and a fixation lamp 11 are provided on the optical path L2 for the fundus observation system and fixation lamp. The SLO scanning unit 4 scans light emitted from the SLO light source 10 and fixation lamp 11 on the fundus Er of the eye E to be inspected. The SLO scanning unit 4 includes an X scanner and Y scanner for scanning the light from the SLO light source 10 and fixation lamp 11 in an X direction and Y direction, respectively. According to the present exemplary embodiment, the X scanner is made up of a polygon mirror used to perform high-velocity scanning while the Y scanner is made up of a galvanometer mirror. However, configurations of the X scanner and Y scanner are not limited to this, and desired configurations can be obtained using any appropriate deflecting mirror or the like.

The lens 5 is driven in an optical axis direction indicated by an arrow in FIG. 2, by a non-illustrated motor controlled by the control apparatus 300. The lens 5 makes up a focus lens used to focus the SLO optical system and fixation lamp 11.

The mirror 7 is made up of a prism on which a perforated mirror or hollow mirror has been deposited and separates illuminating light of the SLO light source 10 and light of the fixation lamp 11 from return light from the fundus Er. Although in the present exemplary embodiment, the SLO light source 10 and the like are provided in a transmission direction of the mirror 7 and the photodiode 9 is provided in a reflection direction, the layout may be reversed.

The third dichroic mirror 8 branches the optical path L2 into an optical path to the SLO light source 10 and an optical path to the fixation lamp 11 according to the wavelength band. In the present exemplary embodiment, the fixation lamp 11 is provided in a transmission direction of the third dichroic mirror 8 and the SLO light source 10 is provided in a reflection direction. However, the fixation lamp 11 and SLO light source 10 may be laid out in the transmission direction and reflection direction of the third dichroic mirror 8 by changing places with each other.

The photodiode 9 detects the return light from the fundus Er of the eye E to be inspected. The photodiode 9 sends an output signal based on the detected light to the control apparatus 300. Based on the signal received from the photodiode 9, the control apparatus 300 can generate a front image of the fundus Er of the eye E to be inspected.

The SLO light source 10 generates light with a wavelength of around 780 nm to be directed at the eye E to be inspected. The fixation lamp 11 generates visible light used to urge the eye E to be inspected to get fixed at any desired position in any desired direction.

Illuminating light emitted from the SLO light source 10 is reflected by the third dichroic mirror 8, and after passing through the mirror 7 and lenses 6 and 5, scanned over the fundus Er of the eye E to be inspected by the SLO scanning unit 4. The return light from the fundus Er retraces the same route as the illuminating light and is then reflected by the mirror 7 and led to the photodiode 9.

The light emitted from the fixation lamp 11 is transmitted through the third dichroic mirror 8 and mirror 7, and after passing through the lenses 6 and 5, scanned over the eye E to be inspected by the SLO scanning unit 4. In so doing, the control apparatus 300 can blink the fixation lamp 11 along with movement of the SLO scanning unit 4 and thereby project a light beam of any desired shape onto any desired position on the eye E to be inspected, urging visual fixation of the person to be inspected.

The optical path L3 for observation of the anterior ocular segment includes a lens 12, a split prism 13, a lens 14, and a CCD 15 for observation of the anterior ocular segment. The split prism 13 is placed at a position conjugate with the pupil of the eye E to be inspected such that a distance in a Z direction (anteroposterior direction) between the eye E to be inspected and the imaging optical system 200 can be detected as a split image of the anterior ocular segment.

The CCD 15 is sensitive to a wavelength of a non-illustrated light source for observation of the anterior ocular segment, specifically to a wavelength of around 970 nm. The CCD 15 sends an output signal based on the detected light to the control apparatus 300. Based on the signal received from the CCD 15, the control apparatus 300 can generate an anterior ocular segment image of the eye E to be inspected.

Next, the OCT optical system used to acquire tomographic information on the fundus Er of the eye E to be inspected will be described. An X-Y scanner 16 and lenses 17 and 18 are installed on the optical path L1 of the OCT optical system.

The X-Y scanner 16 makes up an OCT scanning unit for scanning light from the OCT light source 20 over the fundus Er of the eye E to be inspected. Although the X-Y scanner 16 is illustrated as a single mirror in FIG. 1, the X-Y scanner 16 according to the present exemplary embodiment is made up of galvanometer mirrors for performing scanning in two axial directions-X and Y directions. Note that the configuration of the X-Y scanner 16 is not limited to this, and a desired configuration can be obtained using any appropriate deflecting mirror.

The lens 17 is driven in an optical axis direction indicated by an arrow in FIG. 2, by a non-illustrated motor controlled by the control apparatus 300. The lens 17 makes up a focus lens used to focus the light produced by the OCT light source 20 and emitted from an optical fiber 21 on the eye E to be inspected. As a result of focusing by means of the lens 17, return light from the eye E to be inspected enters a tip of the optical fiber 21 at the same time, being focused into a spot.

Furthermore, the OCT optical system includes an optical coupler 19, an OCT light source 20, optical fibers 21 to 24 connected to the optical coupler 19, a lens 25, dispersion compensation glass 26, a reference mirror 27, and a spectroscope 28.

The light emitted from the OCT light source 20 enters the optical coupler 19 via the optical fiber 22. The optical coupler 19 divides the light from the OCT light source 20 into measuring light and reference light. The measuring light enters the optical path L1 via the optical fiber 21, and then enters the eye E to be inspected through the optical path L1 of the OCT optical system to the objective lens 1. Upon entering the eye E to be inspected, the measuring light is reflected and scattered by the fundus Er and the like, and then reaches the optical coupler 19 as return light through the same optical path. The components passed by the measuring light between the optical fiber 21 and objective lens 1 make up a measuring optical system.

On the other hand, the reference light enters a reference optical system through the optical fiber 23. The reference optical system includes the lens 25, the dispersion compensation glass 26 and the reference mirror 27. The dispersion compensation glass 26 can compensate dispersion of the reference light for dispersion of the measuring light returning by being reflected and scattered by the eye E to be inspected. The reference mirror 27 is held adjustably in an optical axis direction indicated by an arrow in FIG. 2, by a non-illustrated motor and drive mechanism controlled by the control apparatus 300.

The reference light enters the reference mirror 27 through the lens 25 and dispersion compensation glass 26. The reference light reflected by the reference mirror 27 reaches the optical coupler 19 through the same optical path.

The measuring light and reference light reaching the optical coupler 19 in this way are coupled together into interference light. The measuring light and reference light interfere each other when optical path length of the measuring light and optical path length of the reference light become almost equal to each other. Therefore, driving of the reference mirror 27 is controlled by the control apparatus 300 so as to match the optical path length of the reference light to the optical path length of the measuring light which varies with the eye E to be inspected. The interference light generated by the optical coupler 19 is led to the spectroscope 28 through the optical fiber 24. Here, the optical coupler 19 makes up a dividing unit for dividing the light from the OCT light source 20 into measuring light and reference light as well as an interference unit for coupling together the measuring light and reference light to generate interference light.

The spectroscope 28 includes lenses 29 and 31, a diffraction grating 30, and a line sensor 32. The interference light emitted from the optical fiber 24 is converted into parallel light by the lens 29, spectrally separated by the diffraction grating 30, and focused onto the line sensor 32 by the lens 31. The line sensor 32 detects interference light, and sends an interference signal based on the interference light to the control apparatus 300. Based on the interference signal received from the line sensor 32, the control apparatus 300 generates a tomographic image or OCTA image of the eye E to be inspected.

Figure 3:
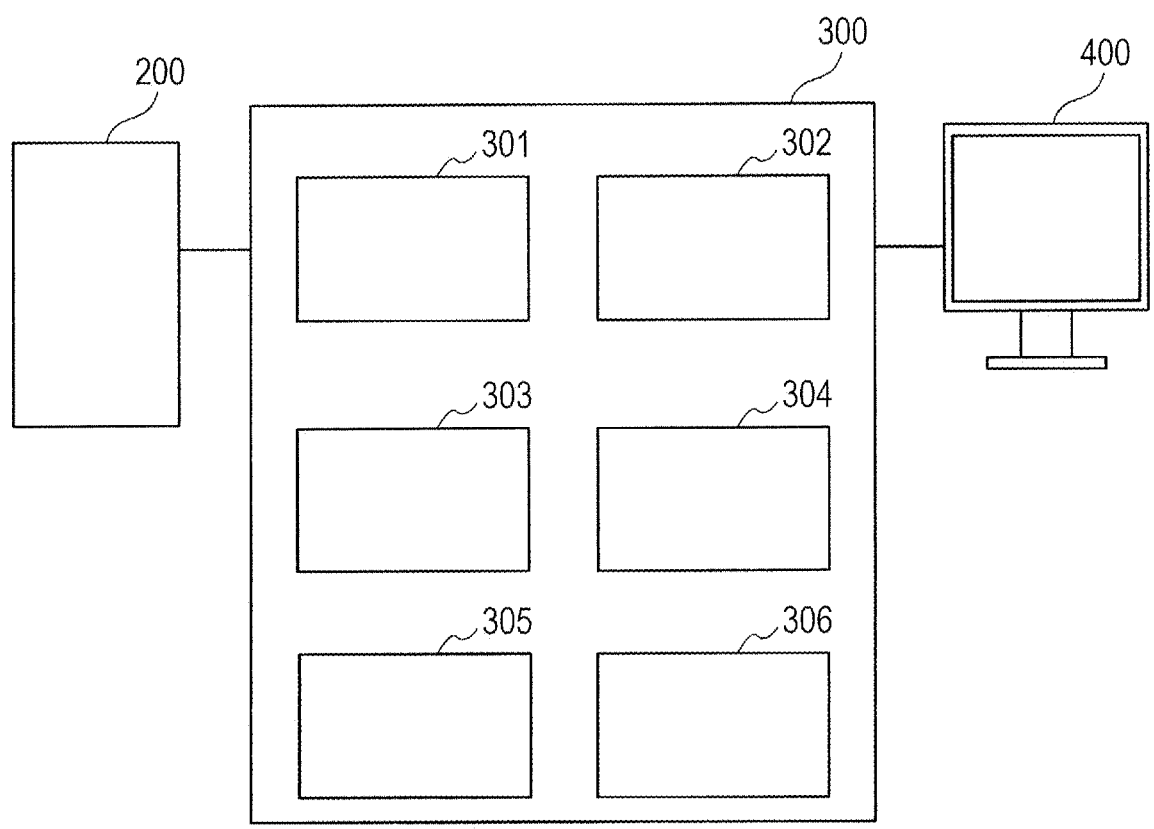
FIG. 3 shows a schematic configuration of a control unit.

Next, a configuration of the control apparatus 300 will be described with reference to FIG. 3. FIG. 3 shows a schematic configuration of the control apparatus 300. The control apparatus 300 includes an acquisition unit 301, an image generating unit 302, a storage unit 303, an OCTA image generating unit 304, a front image generating unit 305 and a control unit 306.

The acquisition unit 301 acquires output signals from the photodiode 9, CCD 15 and line sensor 32 of the imaging optical system 200. Also, the acquisition unit 301 acquires the scanning position and time at which the measuring light was scanned by the X-Y scanner 16 of the imaging optical system 200 from the imaging optical system 200 or control unit 306. Furthermore, the acquisition unit 301 can acquire a signal generated based on the interference signal and subjected to a Fourier transform or the Fourier-transformed signal additionally subjected to some signal processing from the image generating unit 302. Hereinafter, a Fourier-transformed signal corresponding to each pixel position in a tomographic image as well as the Fourier-transformed signal additionally subjected to some signal processing will be referred to as tomographic data. The tomographic data also includes, for example, data obtained by converting Fourier-transformed data into luminance or density information.

The image generating unit 302 generates a fundus front image (SLO image) based on a signal output from the photodiode 9 and acquired by the acquisition unit 301, the signal being output when the fundus Er of the eye E to be inspected was scanned in the X direction and Y direction by the SLO scanning unit 4. Similarly, the image generating unit 302 generates an anterior ocular segment image of the eye E to be inspected based on a signal supplied from the CCD 15 and acquired by the acquisition unit 301.

Also, the image generating unit 302 Fourier-transforms the interference signal supplied from the line sensor 32 and acquired by the acquisition unit 301, converts the resulting data into luminance or density information, and thereby generates an image in a depth direction (Z direction) of the eye E to be inspected. Consequently, the image generating unit 302 acquires a tomographic image in a depth direction (Z direction) at one point in the fundus Er of the eye E to be inspected. This scan method is referred to as an A-scan, and the resulting tomographic image is referred to as an A-scan image.

Plural A-scan images can be acquired by repeating such A-scans while scanning the fundus Er with the measuring light in a predetermined transverse direction using the X-Y scanner 16. For example, the control apparatus 300 can obtain a tomographic image in an X-Z plane by scanning the measuring light in the X direction and obtain a tomographic image in a Y-Z plane by scanning the measuring light in the Y direction. A method of scanning the fundus Er of the eye E to be inspected in a predetermined transverse direction in this way is referred to as a B-scan and the resulting tomographic image is referred to as a B-scan image. Also, a method of scanning in a direction orthogonal to the X-Z plane or Y-Z plane of the B-scan is referred to as a C-scan and a resulting three-dimensional XYZ tomographic image is referred to as a C-scan image.

The storage unit 303 stores various information acquired by the acquisition unit 301 and the SLO images, anterior ocular segment images, two-dimensional or three-dimensional tomographic data (including tomographic images) generated by the image generating unit 302. Also, the storage unit 303 stores the motion contrast data and two-dimensional or three-dimensional motion contrast images generated by the OCTA image generating unit 304 as well as the front images (pseudo-SLO images) generated by the front image generating unit 305. Furthermore, the storage unit 303 stores programs making up components of the control apparatus 300.

Based on the tomographic data acquired from the image generating unit 302 or storage unit 303, the OCTA image generating unit 304 calculates motion contrast data and generates an OCTA image, which is a kind of motion contrast image.

Based on the three-dimensional tomographic data acquired from the image generating unit 302 or storage unit 303, the front image generating unit 305 generates a front image of the fundus Er of the eye E to be inspected.

The control unit 306 controls various components of the imaging optical system 200. Besides, the control unit 306 also functions as a display control unit adapted to cause the display unit 400 to display SLO images, tomographic data, OCTA images, front images and information on the person to be inspected and the like stored in the storage unit 303.

The components of the control apparatus 300 can be made up of modules and the like executed by a CPU or MPU of the control apparatus 300. Also, the components of the control apparatus 300 can be made up of circuits such as ASICs configured to implement specific functions. Note that the storage unit 303 can be configured using any storage medium such as an optical disk or memory.

Processes from observation of the eye E to be inspected as preparation for image-taking through to taking of an OCTA image on the OCT apparatus 100 equipped with the imaging optical system 200, control apparatus 300 and display unit 400 will be described below with reference to FIGS. 4A to 7.

Figure 4A:
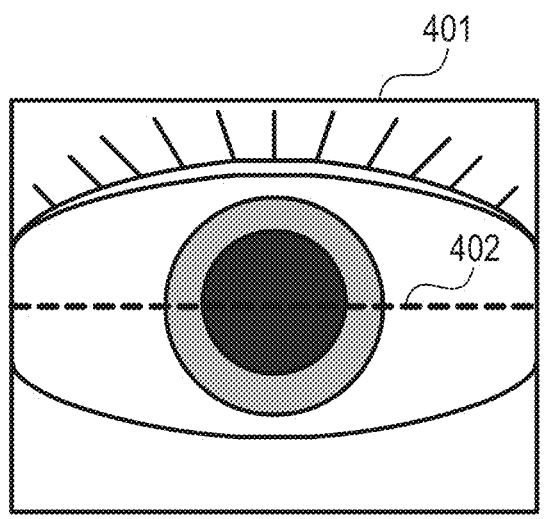
FIG. 4A shows an example of an anterior ocular segment image displayed on a display unit during observation.
Figure 4B:
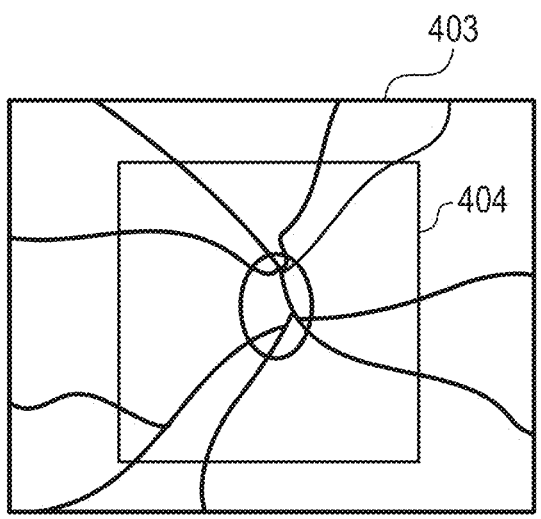
FIG. 4B shows an example of an SLO image displayed on a display unit during observation.

First, observation of the eye E to be inspected as preparation for image-taking will be described with reference to FIGS. 4A and 4B. FIGS. 4A and 4B show examples of an anterior ocular segment image 401 and SLO image 403 displayed on the display unit 400 during observation of the eye E to be inspected.

The eye E to be inspected is positioned in front of the objective lens 1, and the examiner aligns the eye E to be inspected with the imaging optical system 200 in the X, Y, and Z directions using a non-illustrated input unit while watching the anterior ocular segment image 401. Here, the imaging optical system 200 is held, in such a way as to be drivable in the X, Y, and Z directions, by a non-illustrated motor-driven stage controlled by the control apparatus 300, and the examiner can operate and drive the imaging optical system 200 using a non-illustrated input unit connected to the control apparatus 300. Alignment in the X and Y directions is performed such that the pupil center shown in the anterior ocular segment image 401 will lie in the center of a screen in which the anterior ocular segment image 401 is displayed.

Also, a line 402 is shown in the anterior ocular segment image 401. The line 402 is used for alignment between the imaging optical system 200 and eye E to be inspected. More specifically, when the position of the imaging optical system 200 with respect to the eye E to be inspected in the Z-direction (depth direction) is not appropriate, the anterior ocular segment image 401 is split along the line 402 by the split prism 13. The examiner can align the eye E to be inspected with the imaging optical system 200 in the Z direction by controlling driving of the imaging optical system 200 in the Z direction such that the anterior ocular segment image 401 will not be split by the line 402.

Note that the alignment of the imaging optical system 200 with the eye E to be inspected may be performed by the control unit 306 by analyzing the anterior ocular segment image and controlling driving of the motor-driven stage of the imaging optical system 200 according to analysis results.

When the alignment between the eye E to be inspected and imaging optical system 200 in the X, Y, and Z directions is finished, the display unit 400 displays the SLO image 403 generated based on scanning of the illuminating light in the X and Y directions performed by the SLO scanning unit 4. The anterior ocular segment image 401 and SLO image 403 are updated at any time, allowing the examiner to observe the eye E to be inspected without delay.

A scan area 404 in the SLO image 403 is an area scanned during acquisition of tomographic data, and is shown as being superimposed on the SLO image 403. Hereinafter, a B-scan direction, which is a main scanning direction of the OCT apparatus 100, will be designated as an X direction, a C-scan direction, which is a sub-scanning direction, will be designated as a Y direction, and scanning positions (scanning lines) in the scan area 404 will be denoted by Y1 to Ymax. Note that according to the present exemplary embodiment, Ymax=Y300. However, the number of scanning lines is not limited to this, and may be any number based on a desired configuration.

The examiner sets a desired scanning position in the scan area 404 by operating a non-illustrated input unit such as a mouse or touch panel. Here, an input unit used to change the scanning position for the X-Y scanner 16 makes up a scanning position changing unit. These operations end the observation of the eye E to be inspected as preparation for image-taking.

Figure 5:
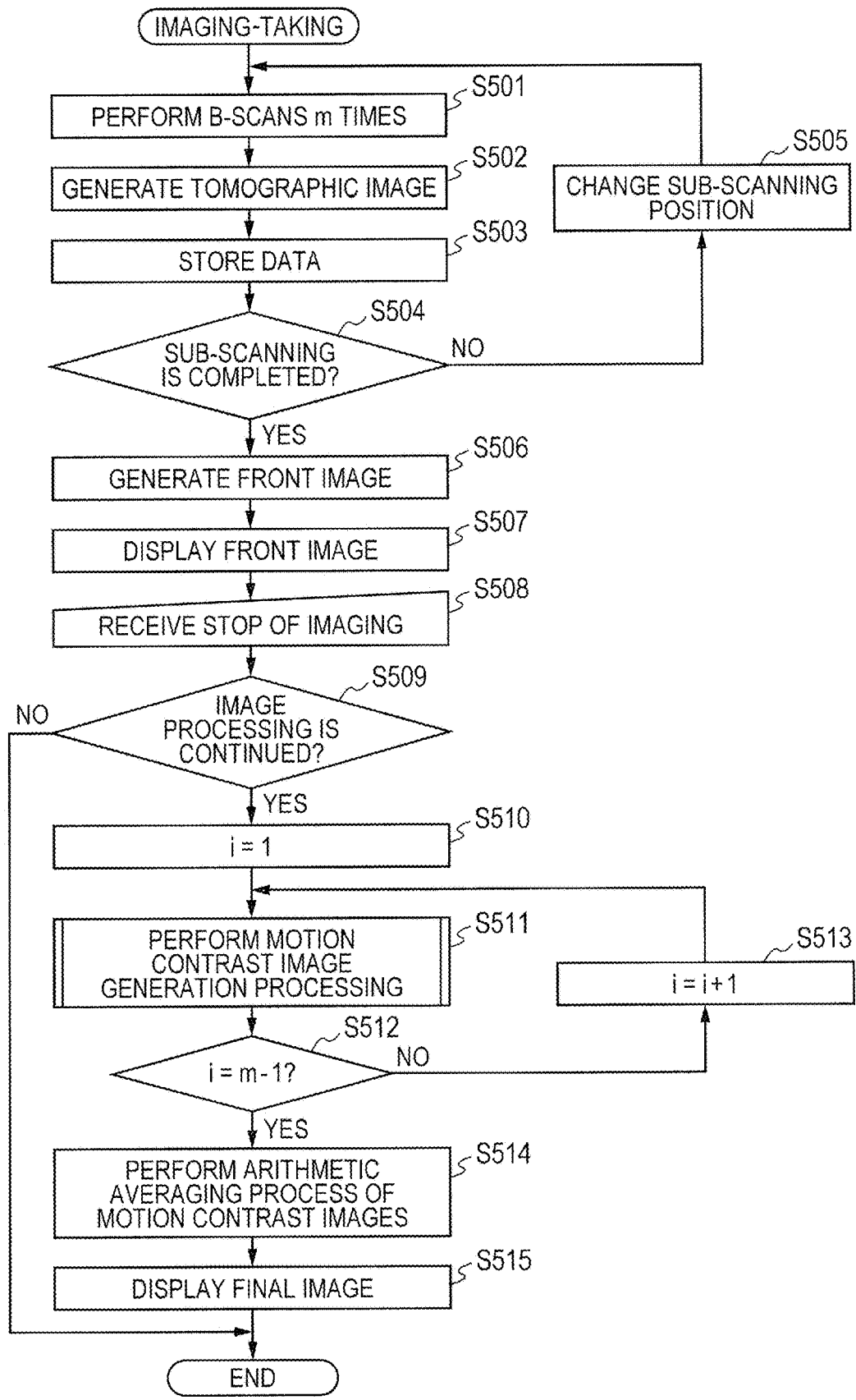
FIG. 5 is a flowchart of an OCTA image-taking process according to a first exemplary embodiment.
Figure 6:
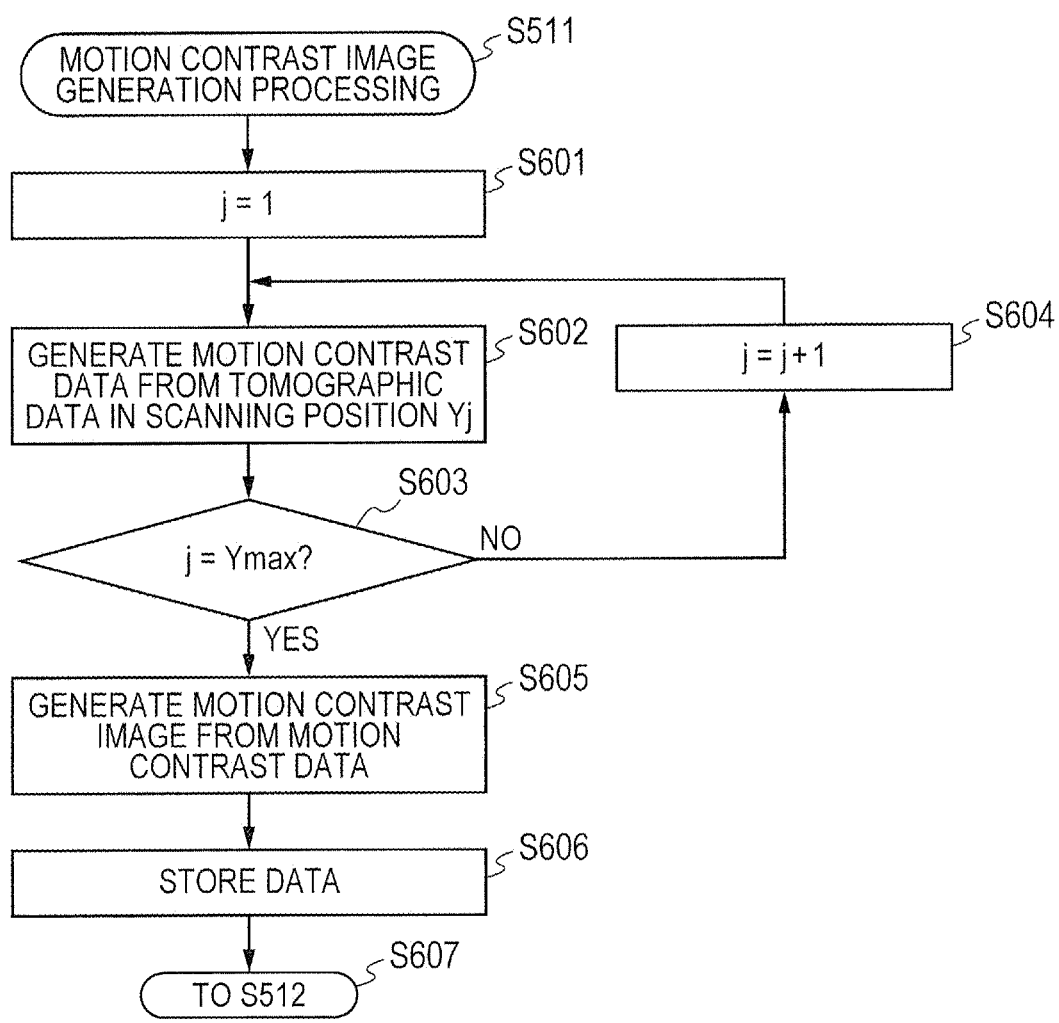
FIG. 6 is a flowchart of a motion contrast image generation process according to the first exemplary embodiment.

Next, taking of an OCTA image will be described with reference to FIGS. 5 and 6. FIG. 5 shows a flowchart of an OCTA image-taking process. FIG. 6 shows a flowchart of a motion contrast image generation process in step S511.

When the control unit 306 detects that a non-illustrated Start Image-Taking button is pressed by the examiner, an OCTA image-taking process is started.

Once the OCTA image-taking process is started, in step S501, the imaging optical system 200 repeatedly scans a scanning position Yn with the measuring light m times set by the examiner in advance. OCTA involves repeating B-scans in substantially the same section, i.e., at substantially the same position, and detecting time variation of the subject among taken images. According to the present exemplary embodiment, m=6, meaning that B-scans are repeated six times at substantially the same position. Note that m, which is the number of times by which B-scans are repeated is not limited to 6, and may be set to any number based on a desired configuration.

In step S502, based on B-scan data of m scans at the scanning position Yn acquired by the acquisition unit 301 from the imaging optical system 200, the image generating unit 302 generates m tomographic images at the scanning position Yn. Specifically, the image generating unit 302 applies background signal subtraction for noise reduction and Fourier transform to each item of B-scan data and generates tomographic data corresponding to each pixel in tomographic images to be generated, and generates the tomographic images using the tomographic data. Note that the tomographic image generation process may be performed using any known processing technique.

In step S503, the storage unit 303 stores data of the m tomographic images generated by the image generating unit 302. In step S504, the control unit 306 determines whether C-scans, i.e., sub-scanning, have been conducted from the scanning position Y1 to the scanning position Ymax. If the control unit 306 determines in step S504 that sub-scanning has not been finished, in step S505, the control unit 306 moves the X-Y scanner 16 of the imaging optical system 200 to a next scanning position and returns the process to step S501. Consequently, the imaging optical system 200 performs main scanning of the eye E to be inspected at a first position with the measuring light m times in succession and then performs main scanning at a second position different from the first position m times in succession. In contrast, if the control unit 306 determines in step S504 that sub-scanning to the scanning position Ymax has been finished, the process moves to step S506. According to the present exemplary embodiment, when the sub-scanning is finished, optical coherence tomography imaging of the eye E to be inspected has been carried out m times at different times and 300 (Ymax) lines×6 times of data have been saved. Note that when the sub-scanning is finished and the process moves to step S506, the image-taking process of the eye E to be inspected is finished and the OCTA image-taking process is continued based on the data acquired in the image-taking process of the eye E to be inspected.

Next, in step S506, the front image generating unit 305 determines average luminance values from three-dimensional tomographic data which is based on the tomographic data acquired as a result of a first scan at each scanning position, and thereby generates a front image of the fundus Er. More specifically, the front image generating unit 305 rearranges items of the three-dimensional tomographic data acquired from the acquisition unit 301 according to the scanning positions and times at which the items of tomographic data have been acquired and identifies the tomographic data (first tomographic data) acquired at each scanning position as a result of the first scan. In relation to the first tomographic data at each scanning position, the front image generating unit 305 determines an average luminance value from A-scan data. Furthermore, the average luminance values determined in relation to the A-scans are established as a pixel value at each pixel position, in the front image, corresponding to the A scan position. Consequently, the front image generating unit 305 can generate a front image based on the tomographic data acquired by the OCT optical system.

Note that although the present exemplary embodiment is configured to generate a front image using average luminance values, the tomographic data used to generate the front image is not limited to average luminance values. The front image may be generated using, for example, the top 10% of A-scan data in terms of luminance or a median of the A-scan data.

In step S507, the control unit 306 displays the generated front image on the display unit 400. In step S508, the control unit 306 receives input via a non-illustrated Stop button. The examiner checks the front image displayed on the display unit 400, determines the success or failure of the image-taking, and presses the Stop Image-Taking button if renewed image-taking is necessary.

In step S509, in response to an output of the Stop Image-Taking button, the control unit 306 determines whether to continue image processing. If the control unit 306 detects that the Stop button is pressed in step S508, the control unit 306 determines in step S509 that image processing is not to be continued and finishes image-taking.

In contrast, if the Stop Image-Taking button is not pressed in step S508 and the control unit 306 determines in step S509 that image processing is to be continued, the process moves to step S510. In step S510, the OCTA image generating unit 304 sets an index i of the three-dimensional tomographic data used for an OCTA image generation process to 1. Hereinafter, the i-th set of three-dimensional tomographic data refers to two-dimensional tomographic data obtained by the i-th B-scans at respective scanning positions and grouped into a set of three-dimensional tomographic data according to the scanning positions. Note that the set of three-dimensional tomographic data refers to a group of tomographic data resulting from arranging two-dimensional tomographic data obtained by conducting one B-scan at each scanning position.

The OCTA image generating unit 304 repeats steps S511 to S513, thereby computationally compares six sets of three-dimensional tomographic data, comparing the first set with the second set, the second set with the third set, the third set with the fourth set, the fourth set with the fifth set, and the fifth set with the sixth set, and generates five motion contrast images.

First, in step S511, the OCTA image generating unit 304 generates an OCTA image, which is a motion contrast image showing the front of the eye E to be inspected, from the i-th set of three-dimensional tomographic data and (i+1)th set of three-dimensional tomographic data.

Now, an OCTA image generation process of the OCTA image generating unit 304 will be described in detail with reference to FIG. 6. When the process moves to step S511, the OCTA image generating unit 304 sets an index j of the scanning position Yj to 1 in step S601 shown in FIG. 6.

In step S602, the OCTA image generating unit 304 generates motion contrast data from the tomographic data acquired as a result of the i-th B-scan and tomographic data acquired as a result of the (i+1)th B-scan at the scanning position Yj. The OCTA image generating unit 304 calculates differences between corresponding portions of two sets of tomographic data to be compared, thereby calculates changes between the two sets of tomographic data, and thereby generates motion contrast data.

Note that according to the present exemplary embodiment, the OCTA image generating unit 304 calculates differences between sets of tomographic data using total values of tomographic data at A-scan positions. However, the data used in generating motion contrast data is not limited to the total values of tomographic data at A-scan positions, and average values, medians or the like may be used. Here, the motion contrast data at each scanning position Yj corresponds to one line of pixel values in the OCTA image, which is a front image of the fundus Er.

In step S603, the OCTA image generating unit 304 determines whether the index j has reached Ymax. If the OCTA image generating unit 304 determines in step S603 that the index j has not reached Ymax, the process moves to step S604. In step S604, the OCTA image generating unit 304 increments the index j by 1 and returns the process to step S602.

If the OCTA image generating unit 304 determines in step S603 that the index j has reached Ymax, the process moves to step S605. In step S605, the OCTA image generating unit 304 generates an OCTA image, which is a motion contrast image, using motion contrast data corresponding to each scanning position as pixel values on each line.

In step S606, the storage unit 303 stores the generated OCTA image data. Subsequently, the process moves to step S607, and then to step S512 shown in FIG. 5.

In step S512, the OCTA image generating unit 304 determines whether the index i has reached m−1. If the OCTA image generating unit 304 determines in step S512 that the index i has not reached m−1, the process moves to step S513. In step S513, the OCTA image generating unit 304 increments the index i by 1 and returns the process to step S511.

Figure 7:
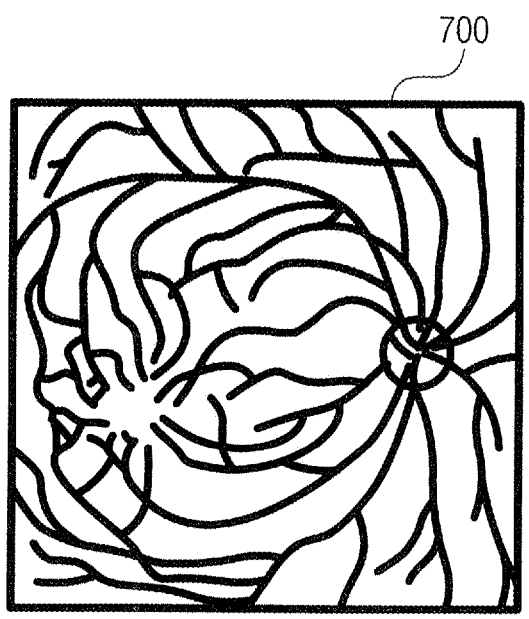
FIG. 7 shows an example of an average OCTA image generated.

In step S512, if the OCTA image generating unit 304 determines that the index i has reached m−1, the process moves to step S514. In step S514, the OCTA image generating unit 304 performs an arithmetic averaging process of generated m−1 motion contrast images and thereby generates an averaged OCTA image (average OCTA image). FIG. 7 shows an example of an average OCTA image. By averaging plural OCTA images, noise can be reduced and a clear OCTA image 700 such as shown in FIG. 7 can be generated. Note that averaging of OCTA images is sufficient if noise reduction can be achieved, and that averaging may be done based on a median calculation, mode calculation or the like other than an arithmetic average (arithmetic mean).

Finally, in step S515, the control unit 306 displays the generated average OCTA image as a final image on the display unit 400, notifies the examiner about the completion of image-taking, and thereby finishes the image-taking process. Although in the present exemplary embodiment, notification about completion of image-taking is given via a display on the display unit 400, the notification may be given as a notification sound from a speaker provided separately or lighting of an LED provided separately. Note that in a display area of the display unit 400 in which a front image is displayed, the control unit 306 can cause the display unit 400 to display an average OCTA image by changing from the front image. Also, the control unit 306 may display the front image and average OCTA image in separate display areas of the display unit 400.

As described above, the OCT apparatus 100 according to the present exemplary embodiment includes the imaging optical system 200 that performs optical coherence tomography imaging of the eye E to be inspected multiple times at different times. More specifically, the imaging optical system 200 performs optical coherence tomography imaging of the eye E to be inspected multiple times at different times using measuring light controlled to perform main scanning of the subject at a first position multiple times in succession and then perform main scanning at a second position different from the first position multiple times in succession. Also, the OCT apparatus 100 includes the control apparatus 300 connected to the imaging optical system 200 in a communication-ready state and configured to process images generated from three-dimensional tomographic data obtained using results of optical coherence tomography imaging performed multiple times. The control apparatus 300 includes the acquisition unit 301 configured to acquire multiple sets of three-dimensional tomographic data obtained by scanning the eye E to be inspected at each scanning position with the measuring light multiple times in succession. Also, the control apparatus 300 includes the front image generating unit 305 configured to generate a front image using at least one of the multiple sets of three-dimensional tomographic data. Furthermore, the control apparatus 300 includes the OCTA image generating unit 304 configured to generate a motion contrast image using the multiple sets of three-dimensional tomographic data and the control unit 306 configured to display a front image on the display unit 400 before the motion contrast image is displayed.

The front image generating unit 305 generates a front image using one of the multiple sets of three-dimensional tomographic data. Note that in that display area of the display unit 400 in which the front image is displayed, the control unit 306 can display a motion contrast image by changing from the front image. The OCTA image generating unit 304 calculates differences among temporally successive items of three-dimensional tomographic data and generates a motion contrast image using the differences. Also, the OCTA image generating unit 304 generates an averaged image of plural motion contrast images generated using multiple sets of three-dimensional tomographic data including three or more sets of three-dimensional tomographic data and the control unit 306 displays the averaged image on the display unit 400.

With this configuration, the OCT apparatus 100 according to the present exemplary embodiment displays a front image based on tomographic data before displaying a motion contrast image. The front image can be generated with a smaller amount of calculation and far shorter processing time than the motion contrast image generated by calculating motion contrast data. Therefore, the OCT apparatus 100 according to the present exemplary embodiment can display the front image based on tomographic data at an early stage after image-taking to determine the success or failure of the image-taking. This allows waiting time for renewed image-taking to be reduced and enables reducing burdens on the person to be inspected and examiner.

Also, the imaging optical system 200 according to the present exemplary embodiment includes an SLO optical system (frontal view acquisition unit) configured to acquire information on a frontal view (for example, the fundus) of the eye E to be inspected. In this case, the acquisition unit 301 may acquire frontal view information from the imaging optical system 200 and the control unit 306 may display an SLO image (second front image) generated from the frontal view information on the display unit 400 during scanning with measuring light. With this configuration, by displaying the SLO image based on information acquired by the SLO optical system which shares part of optical components such as the objective lens with the OCT optical system, the examiner can get a rough idea of circumstances including the position of the eye E to be inspected at the time of acquisition of tomographic data. Consequently, if an input of a command to stop image processing is accepted according to the SLO image, the success or failure of image-taking can be determined even during the image-taking, allowing the waiting time for renewed image-taking to be further reduced and enabling further reduction in the burdens on the person to be inspected and examiner.

Although the present exemplary embodiment is configured such that a determination as to whether to stop image processing is made only after a front image is displayed, by handling an input of a command to stop image processing as an interrupt input to the control unit 306, the processing may be allowed to be stopped immediately.

Also, although the present exemplary embodiment is configured to generate a front image after tomographic data used to generate an OCTA image is acquired through m B-scans, the timing to generate a front image is not limited to this. For example, the front image generating unit 305 may generate a front image immediately after all the tomographic data used to generate the front image has been acquired. Specifically, according to the present exemplary embodiment, the front image generating unit 305 may generate a front image immediately after the first B-scan at the last scanning position (Ymax) in order to generate a front image based on the tomographic data acquired through the first B-scan at each scanning position. Furthermore, the front image generating unit 305 may generate a front image concurrently with scanning by generating image data at the pixel position corresponding to each scanning position after the first B-scan at the scanning position. This allows the front image to be generated and displayed at an earlier stage, and thus the success or failure of image-taking can be determined at an earlier stage, thereby allowing the waiting time for renewed image-taking to be further reduced and enabling further reduction in the burdens on the person to be inspected and examiner.

Note that the front image generating unit 305 is not limited to a configuration in which a front image is generated from tomographic data acquired through the first B-scans, and a front image may be generated from tomographic data acquired through second, third, or any other B-scans. Also, the front image generating unit 305 may generate a front image using different sets of tomographic data. For example, the front image generating unit 305 may generate an upper half of a front image using tomographic data acquired through the first B-scans, and generate a lower half using tomographic data acquired through the second B-scans. Note that as described above, the front image generating unit 305 can generate a front image with a far shorter processing time than the motion contrast image generated by calculating motion contrast data. Therefore, even when a front image is generated using some or all of multiple sets of three-dimensional tomographic data, the front image can be generated with a smaller amount of calculation and far shorter processing time than when a motion contrast image is generated using all of multiple sets of three-dimensional tomographic data. Thus, even in such a case, the front image can be displayed based on tomographic data at an early stage after image-taking to determine the success or failure of the image-taking.

Also, although in the present exemplary embodiment, a motion contrast image (OCTA image) generation process is started based on a determination as to whether to continue image processing made after a front image is displayed, the timing to start the motion contrast image generation process is not limited to this. For example, the motion contrast image may be generated concurrently with the generation of a front image. Even in this case, because a front image generation process is finished earlier than the motion contrast image generation process, the front image can be displayed earlier than the motion contrast image. This allows the examiner to determine the success or failure of image-taking at an early stage after the image-taking. Note that in this case, the control apparatus 300 can be configured to interrupt the motion contrast image generation process and terminate taking of the motion contrast image if the Stop Image-Taking button is pressed by the examiner based on the front image.

Second Exemplary Embodiment

The first exemplary embodiment is configured to generate an average OCTA image based on m OCTA images and then display the OCTA image. In contrast, an OCT apparatus according to a second exemplary embodiment generates and displays average image of already generated OCTA images when generating each OCTA image and thereby reduces the time required to display the OCTA image.

Figure 8:
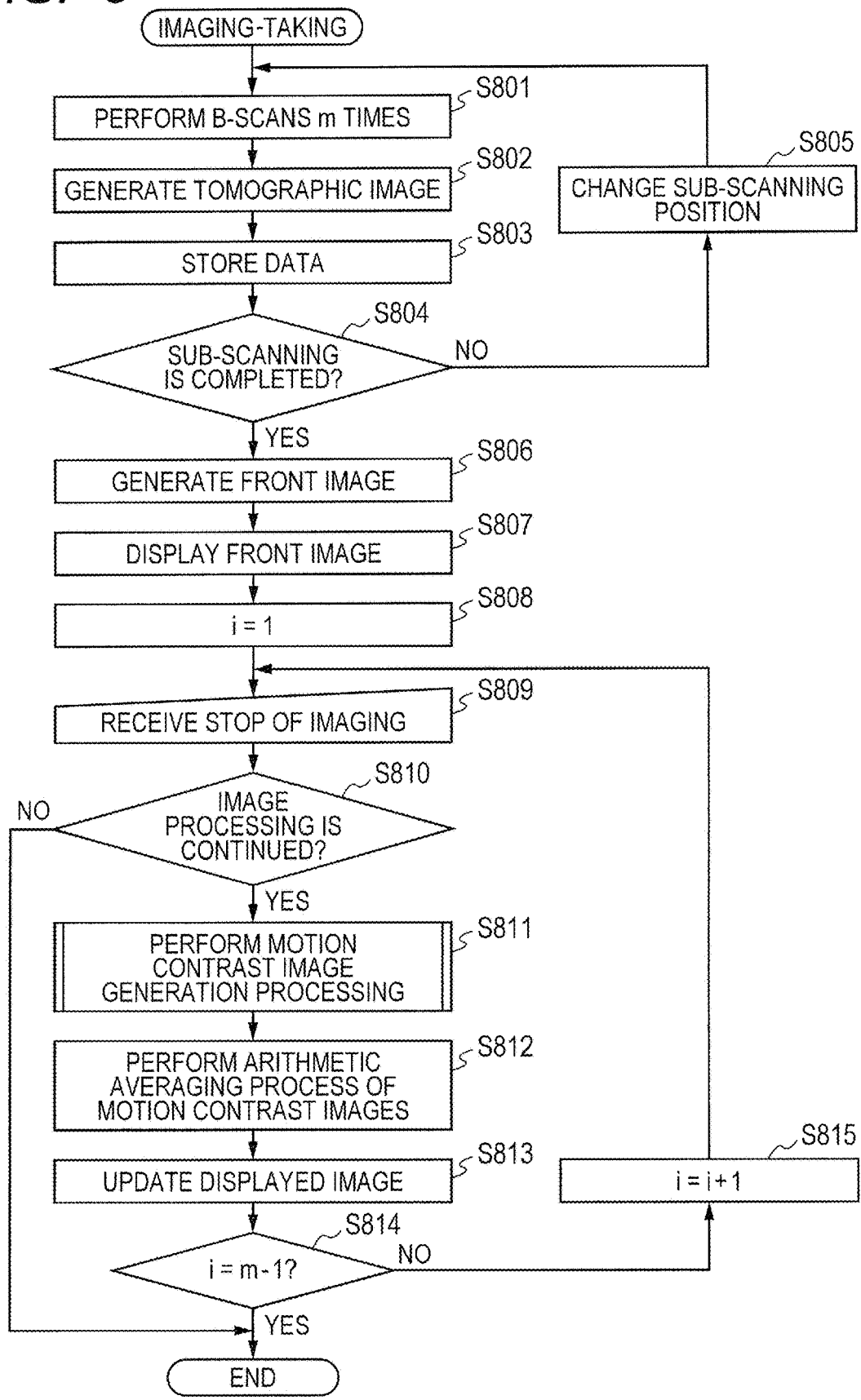
FIG. 8 is a flowchart of an OCTA image-taking process according to a second exemplary embodiment.
Figure 9A:
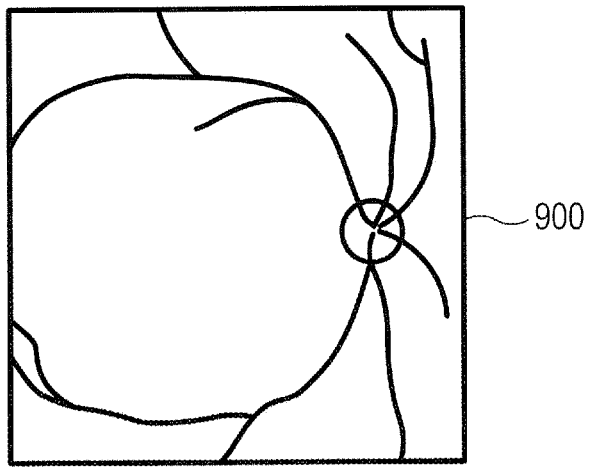
FIG. 9A shows an example of a front image according to the second exemplary embodiment.
Figure 9B:
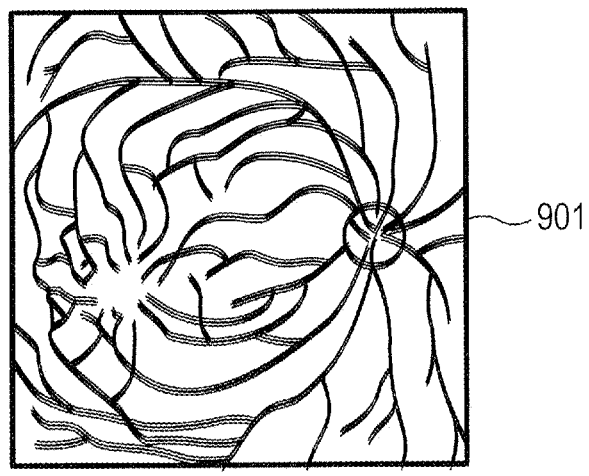
FIG. 9B shows an example of an average OCTA image according to the second exemplary embodiment.
Figure 9C:
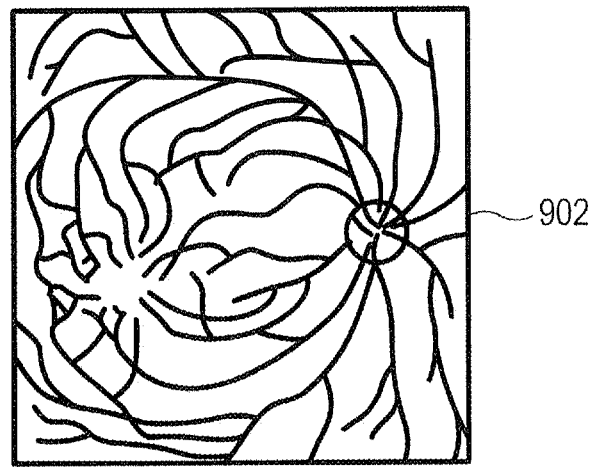
FIG. 9C shows an example of an average OCTA image according to the second exemplary embodiment.

The OCT apparatus according to the present exemplary embodiment will be described below with reference to FIGS. 8 and 9C. A configuration of the OCT apparatus according to the present exemplary embodiment is similar to that of the OCT apparatus 100 according to the first exemplary embodiment, and thus components are denoted by the same reference numerals as the corresponding components, and description thereof will be omitted. The OCT apparatus according to the present exemplary embodiment will be described below by focusing on differences from the OCT apparatus 100 according to the first exemplary embodiment. Note that according to the present exemplary embodiment, again m=6.

First, an OCTA image-taking process according to the present exemplary embodiment will be described with reference to FIG. 8. FIG. 8 is a flowchart of the OCTA image-taking process according to the present exemplary embodiment.

The processes of step S801 to step S807 are similar to the processes of step S501 to step S507 according to the first exemplary embodiment, and thus description thereof will be omitted. When the display unit 400 displays a front image in step S807, the process moves to step S808. In step S808, the OCTA image generating unit 304 sets the index i of the three-dimensional tomographic data used for an OCTA image generation process to 1 as with step S510 of the first exemplary embodiment.

Next, in step S809 and step S810, as with step S508 and step S509 of the first exemplary embodiment, the control unit 306 receives input via a non-illustrated Stop button and determines whether to continue image processing. If it is determined in step S810 that image processing is not to be continued, the control unit 306 finishes the image-taking process.

In contrast, if the control unit 306 determines in step S810 that image processing is to be continued, the process moves to step S811. In step S811, as with step S511 of the first exemplary embodiment, the OCTA image generating unit 304 generates an OCTA image, which is a motion contrast image, from the i-th set of three-dimensional tomographic data and (i+1)th set of three-dimensional tomographic data.

Next, in step S812, the OCTA image generating unit 304 performs an arithmetic averaging process of already generated OCTA images and thereby generates an average OCTA image based on the already generated OCTA images. For example, if i=3, the OCTA image generating unit 304 performs an arithmetic averaging process of already generated three OCTA images and thereby generates an average OCTA image based on the already generated three OCTA images. Note that if i=1 in step S812, the first OCTA image generated becomes an average OCTA image as it is.

Subsequently, in step S813, the control unit 306 updates the OCTA image to be displayed on the display unit 400 with the average OCTA image generated in step S812, and displays the newly generated average OCTA image on the display unit 400. That is, on the display unit 400, the control unit 306 can display the average OCTA image in a display area for use to display average OCTA images, by switching to newly generated average OCTA images one after another.

In step S814, the OCTA image generating unit 304 determines whether the index i has reached m−1. If the OCTA image generating unit 304 determines in step S814 that the index i has not reached m−1, the process moves to step S815. In step S815, the OCTA image generating unit 304 increments the index i by 1 and returns the process to step S809.

If it is determined in step S814 that the index i has reached m−1, the OCTA image generating unit 304 notifies the examiner about the completion of image-taking and finishes the image-taking process. Through the above process, each time a motion contrast image is generated, the OCT apparatus according to the present exemplary embodiment updates the average OCTA image displayed on the display unit 400 and allows the examiner to determine the success or failure of image-taking at an earlier stage based on the OCTA image.

The images displayed on the display unit 400 in the OCTA image-taking process according to the present exemplary embodiment will be described with reference to FIGS. 9A to 9C. FIG. 9A shows an example of a front image 900 generated by the front image generating unit 305. FIG. 9B shows an example of an average OCTA image 901 generated when i=2 and displayed on the display unit 400. FIG. 9C shows an example of an average OCTA image 902, which is a final image, generated when i=5 and displayed on the display unit 400. The average OCTA image 901, which is calculated by averaging a smaller number of OCTA images than the average OCTA image 902 which is a final image, becomes a rather indistinct image.

Since the display unit 400 displays the front image 900 in step S807, the examiner can determine the success or failure of the image-taking based on an image-taking position at an early stage. In addition, according to the present exemplary embodiment, in step S813, the display unit 400 updates the displayed OCTA image such as the average OCTA image 901 or 902 as required each time an OCTA image is generated, and thereby allows the examiner to determine the success or failure of the image-taking based on the OCTA image at an early stage.

Figure 10A:
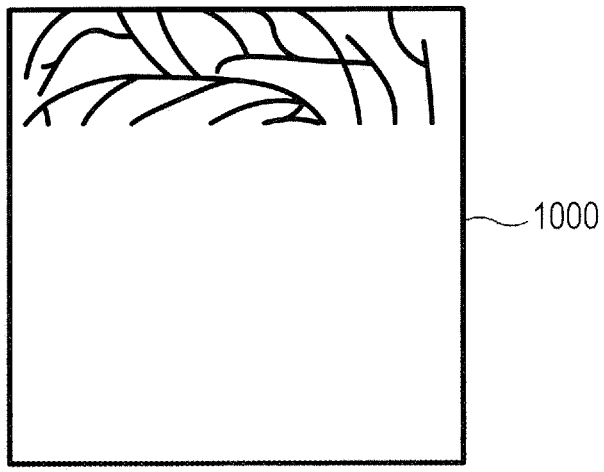
FIG. 10A shows an example of an OCTA image displayed on a conventional OCT apparatus.
Figure 10B:
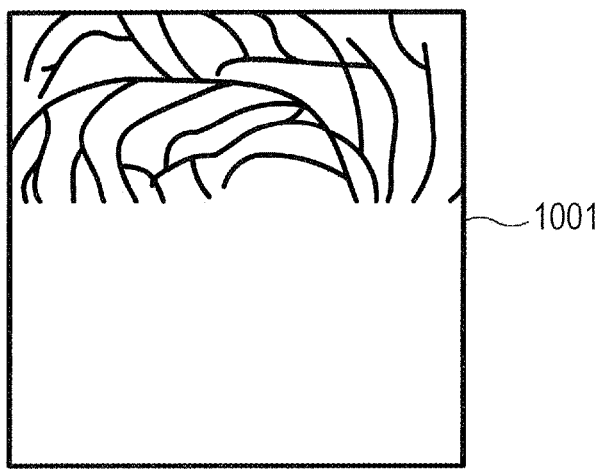
FIG. 10B shows an example of an OCTA image displayed on a conventional OCT apparatus.
Figure 10C:
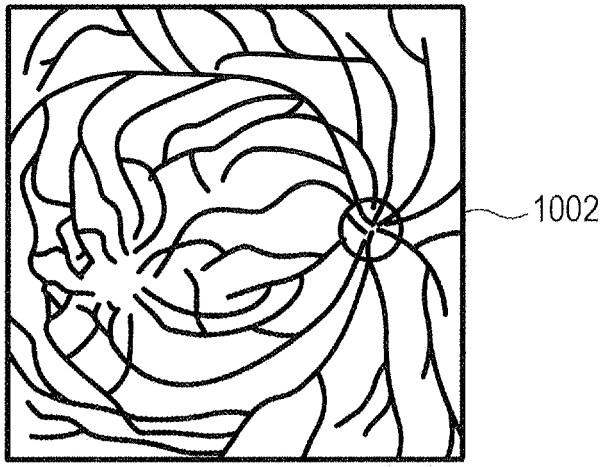
FIG. 10C shows an example of an OCTA image displayed on a conventional OCT apparatus.

Thus, in the OCT apparatus according to the present exemplary embodiment, each time a motion contrast image is generated, the OCTA image generating unit 304 generates an averaged image of already generated motion contrast images in sequence. Then, on the display unit 400, each time the OCTA image generating unit 304 generates an averaged image, the control unit 306 displays the averaged image in a display area for use to display averaged images by switching to the newly generated averaged image. Therefore, the OCT apparatus according to the present exemplary embodiment can display images on the display unit 400 by gradually reducing noise. Consequently, the examiner can determine the success or failure of image-taking at an early stage, based not only on the image-taking position, but also, for example, on changes in an environment. Also, OCTA images of the entire scan area can be displayed at an earlier stage than conventional displays such as shown in FIGS. 10A to 10C. Therefore, the OCT apparatus according to the present exemplary embodiment can identify an abnormal area regardless of the position in the scan area, allowing the success or failure of image-taking to be determined at an early stage over the entire scan area.

Although the present exemplary embodiment is configured such that a determination as to whether to stop image processing is made each time the displayed average OCTA image is updated, by handling an input of a command to stop image processing as an interrupt input to the control unit 306, the processing may be allowed to be stopped immediately.

Also, although the present exemplary embodiment allows the success or failure of the first image-taking to be determined by displaying a front image before displaying a motion contrast image, the image displayed at an early stage to determine the success or failure of image-taking is not limited to a front image. For example, by displaying the first OCTA image on the display unit 400 before displaying an average OCTA image without generating and displaying a front image, OCTA images of the entire scan area can be displayed at an earlier stage than conventional displays. Therefore, the control unit 306 may be configured to display a motion contrast image on the display unit 400 before displaying an average image of motion contrast images without displaying a front image. Even in that case, a motion contrast image based on tomographic data may be displayed to determine the success or failure of image-taking at an early stage after the image-taking. This allows waiting time for renewed image-taking to be reduced and enables reducing the burdens on the person to be inspected and examiner.

Third Exemplary Embodiment

In an OCTA image generation process, the OCTA image generating unit according to each of the first and second exemplary embodiments generates motion contrast data based on all the tomographic data at all the A-scan positions. In contrast, an OCTA image generating unit according to a third exemplary embodiment generates motion contrast data in an OCTA image generation process, based on tomographic data excluding tomographic data of layer regions irrelevant to OCTA image generation and thereby performs an OCTA image generation process at a faster pace.

A configuration of the OCT apparatus according to the present exemplary embodiment is similar to that of the OCT apparatus 100 according to the first exemplary embodiment, and thus components are denoted by the same reference numerals as the corresponding components, and description thereof will be omitted. The OCT apparatus according to the present exemplary embodiment will be described below by focusing on differences from the OCT apparatus 100 according to the first exemplary embodiment.

The control unit 306 of the control apparatus 300 according to the present exemplary embodiment has a function of a tomographic data analysis unit in addition to the function according to the first exemplary embodiment. The control unit 306 recognizes layers of the tomographic images generated by the image generating unit 302, identifies tomographic data excluding tomographic data of the vitreous body and sclera irrelevant to OCTA image generation, and stores the identified tomographic data in the storage unit 303.

More specifically, the control unit 306 generates images by applying a median filter and Sobel filter to respective tomographic images (hereinafter also referred to as a median image and Sobel image, respectively). Next, from the generated median image and Sobel image, the control unit 306 generates a profile for each item of data corresponding to an A-scan. The generated profiles are luminance value profiles in the case of a median image, and gradient profiles in the case of a Sobel image. Then, the control unit 306 detects peaks in the profiles generated from the Sobel image. The control unit 306 extracts boundaries between regions in the retinal layers by referring to median image profiles corresponding to preceding and succeeding regions of detected peaks and peak-to-peak intervals. Then, the control unit 306 recognizes the layers using the boundaries between regions, a template of a fundus structure, and the like.

Among the layers recognized in this way, the control unit 306 identifies tomographic data excluding tomographic data of the vitreous body and sclera irrelevant to OCTA image generation, and stores the identified tomographic data in the storage unit 303. Note that the technique for layer recognition is not limited to the one described above, and may be any of known techniques.

By generating OCTA images from the tomographic data identified by the control unit 306, the OCTA image generating unit 304 can generate the OCTA images with a smaller amount of calculation and perform an OCTA image generation process at a faster pace. Consequently, the OCT apparatus according to the present exemplary embodiment can reduce the time required to display the average OCTA image.

As described above, in the OCT apparatus according to the present exemplary embodiment, the control unit 306 functions as an analysis unit configured to analyze three-dimensional tomographic data. Using layer information recognized by the control apparatus 300 by analyzing three-dimensional tomographic data, the OCTA image generating unit 304 identifies the tomographic data to be used to calculate differences among three-dimensional tomographic data and generates OCTA images. This allows the OCT apparatus according to the present exemplary embodiment to generate OCTA images with a smaller amount of calculation, perform an OCTA image generation process at a faster pace, and thereby reduce the time required to display the final image.

The present exemplary embodiment is configured such that tomographic data excluding tomographic data of the vitreous body and sclera irrelevant to OCTA image generation is identified by the control unit 306 and used to generate OCTA images. However, the identification of the tomographic data to be used for OCTA image generation is not limited to this. The control unit 306 may recognize an observation position by means of layer recognition and exclude data other than data of an area around a site marked for observation set by the examiner in advance from the tomographic data to be used for OCTA image generation. For example, the control unit 306 may identify tomographic data of an area around the optic disk or tomographic data of an area around the macula retinae as tomographic data for use in OCTA image generation, thereby excluding tomographic data of other areas.

Note that although in the present exemplary embodiment, the control unit 306 does layer recognition based on the tomographic images generated by the image generating unit 302, the information used for layer recognition is not limited to this. The control unit 306 can do layer recognition based on the three-dimensional tomographic data acquired by the acquisition unit 301. Therefore, the control unit 306 may do layer recognition using data resulting from a Fourier transform of an interference signal or using a signal resulting from application of some signal processing to this data. Note that the tomographic images generated by the image generating unit 302 are also included in three-dimensional tomographic data because the images are also based on the data resulting from a Fourier transform of an interference signal.

Also, according to the first to third exemplary embodiments, the acquisition unit 301 acquires the interference signal acquired by the imaging optical system 200 and a tomographic signal generated by the image generating unit 302. However, the configuration in which the acquisition unit 301 acquires these signals is not limited to this. For example, the acquisition unit 301 may acquire these signals from a server or imaging apparatus connected with the control apparatus 300 via a LAN, a WAN, the Internet or the like.

Although a Michelson interference system is used in the exemplary embodiments described above, a Mach-Zehnder interference system may be used. For example, depending on the light amount difference between measuring light and reference light, the Mach-Zehnder interference system may be used when the light amount difference is large while using Michelson interference system when the light amount difference is relatively small. Also, although a fiber optical system made up of an optical coupler as a dividing unit is used, a space optical system made up of a collimator and beam splitter may be used. Also, the configuration of the imaging optical system 200 is not limited to the one described above, and part of the components of the imaging optical system 200 may be configured separately from the imaging optical system 200.

Furthermore, although in the exemplary embodiments described above, a spectral domain OCT (SD-OCT) apparatus using an SLD as a light source has been described as an OCT apparatus, the OCT apparatus according to the disclosure is not limited to this. The disclosure is also applicable to any other type of OCT apparatus such as a swept source OCT (SS-OCT) apparatus using a wavelength-swept light source capable of sweeping a wavelength of emergent light or a polarization-sensitive OCT apparatus. Also, when a polarization-sensitive OCT apparatus is used, the OCTA image generating unit 304 may calculate motion contrast data from phase differences or vector differences of complex OCT signals, and complex OCT signals and the like are also included in tomographic data herein.

Note that in the exemplary embodiments described above, the OCTA image generating unit 304 configured to generate OCTA images has been described as a motion contrast image generating unit configured to generate motion contrast images. However, the images generated by motion contrast image generating unit are not limited to OCTA images, and may be, for example, three-dimensional motion contrast images or an averaged image thereof. In that case, the display unit 400 can display three-dimensional motion contrast images or an averaged image of the three-dimensional motion contrast images instead of OCTA images.

Also, although in the exemplary embodiments described above, the fundus Er of the eye E to be inspected has been taken as an example of a subject. For example, the subject may be the anterior ocular segment of the eye E to be inspected or the skin or an organ of the person to be inspected. In that case, the disclosure can be applied to medical equipment such as an endoscope as well as to ophthalmological equipment. Also, the layer recognition according to the third exemplary embodiment can be done according to a structure of the subject.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-005940, filed Jan. 17, 2017 which is hereby incorporated by reference herein in its entirety.

What is claimed is:

1. An image processing apparatus that processes an image generated using at least one item of three-dimensional tomographic data out of a plurality of items of three-dimensional tomographic data obtained by conducting a plurality of optical coherence tomography scans of a subject at different times using measuring light controlled to scan a same position of the subject, the image processing apparatus comprising:
    at least one of (a) at least one processor executing memory-stored instructions and (b) circuitry, configured to function as a plurality of units comprising:
    (1) a front image generating unit configured to generate a front image of the subject using the at least one item of three-dimensional tomographic data;
    (2) a motion contrast image generating unit configured to generate a motion contrast image of the subject using the plurality of items of three-dimensional tomographic data; and
    (3) a display control unit configured to display the front image on a display unit before displaying the motion contrast image.

2. The image processing apparatus according to claim 1, wherein in that display area of the display unit in which the front image is displayed, the display control unit displays the motion contrast image by changing from the front image.

3. The image processing apparatus according to claim 1, wherein in that display area of the display unit in which the front image is displayed, the display control unit displays the motion contrast image by changing from the front image after the motion contrast image is generated.

4. The image processing apparatus according to claim 1, wherein the motion contrast image generating unit calculates a difference between temporally successive items of three-dimensional tomographic data and generates the motion contrast image using the difference.

5. The image processing apparatus according to claim 1, wherein:
the plurality of items of three-dimensional tomographic data includes three or more items of three-dimensional tomographic data;
the motion contrast image generating unit generates an averaged image of a plurality of the motion contrast images generated using the plurality of items of three-dimensional tomographic data; and
the display control unit displays the averaged image on the display unit.

6. The image processing apparatus according to claim 5, wherein:
each time a motion contrast image is generated, the motion contrast image generating unit generates an averaged image of already generated motion contrast images in sequence; and
on the display unit, each time an averaged image is generated, the display control unit displays the averaged image in a display area for use to display averaged images by switching to the newly generated averaged image.

7. The image processing apparatus according to claim 1, wherein the plurality of units further comprises an analysis unit configured to analyze, by recognizing later information, at least one item of three-dimensional tomographic data out of the plurality of items of the three-dimensional tomographic data, and
wherein the motion contrast image generating unit identifies tomographic data to be used to generate the motion contrast image, using the recognized layer information.

8. The image processing apparatus according to claim 7, wherein:
the subject is an eye to be inspected; and
the motion contrast image generating unit identifies tomographic data of an area around the optic disk or tomographic data of an area around the macula retinae as the tomographic data to be used to generate the motion contrast image.

9. The image processing apparatus according to claim 1, wherein the plurality of items of three-dimensional tomographic data is obtained using the measuring light controlled to perform main scanning of the subject at a first position a plurality of times in succession and then perform main scanning at a second position different from the first position a plurality of times in succession.

10. The image processing apparatus according to claim 1, wherein:
the image processing apparatus is connected to an imaging apparatus in a communication-ready state, the imaging apparatus being arranged to perform optical coherence tomography imaging of the subject;
the imaging apparatus includes a frontal view acquisition unit configured to acquire information on a frontal view of the subject;
the image processing apparatus acquires the information on the frontal view from the imaging apparatus; and
the display control unit displays a second front image generated from the information on the frontal view, during scanning with the measuring light.

11. The image processing apparatus according to claim 1, wherein the front image generating unit generates the front image using one item of the three-dimensional tomographic data out of the plurality of items of three-dimensional tomographic data.

12. The image processing apparatus according to claim 1, wherein the motion contrast image generating unit stops generating the motion contrast image on command from an examiner.

13. The image processing apparatus according to claim 1, wherein the display control unit displays a first front image which is the generated front image on the display unit before displaying a second front image which is a different kind of image from the first front image and is the motion contrast image.

14. The image processing apparatus according to claim 1, wherein the motion contrast image generating unit generates the motion contrast image by using differences between temporally successive plural items of the plurality of items of three-dimensional tomographic data.

15. A system comprising: the image processing apparatus according to claim 1; and an optical coherence tomography apparatus including a detector arranged to detect an interference light obtained by coupling (a) a reference light and (b) a return light from the subject irradiated with the measuring light.

16. The image processing apparatus according to claim 7, wherein the motion contrast image generating unit identifies the tomographic data to be used to generate the motion contrast image, using the recognized layer information and an observation site set by an examiner.

17. The image processing apparatus according to claim 1, wherein the display control unit displays the front image or the motion contrast image on the display unit for determination of success or failure of acquiring of tomographic data to be used for generating the motion contrast image.

18. The image processing apparatus according to claim 1, wherein the display control unit displays, on the display unit, a button for reacquiring of tomographic data to be used for generating the motion contrast image.

19. An image processing apparatus that processes an image generated using at least one item of three-dimensional tomographic data out of a plurality of items of three-dimensional tomographic data obtained by conducting a plurality of optical coherence tomography scans of a subject at different times using measuring light controlled to scan a same position of the subject, the image processing apparatus comprising:
at least one of (a) at least one processor executing memory-stored instructions and (b) circuitry, configured to function as a plurality of units comprising:
(1) a front image generating unit configured to generate a front image of the subject using the at least one item of three-dimensional tomographic data;
(2) a motion contrast image generating unit configured to generate a motion contrast image of the subject using the plurality of items of three-dimensional tomographic data; and
(3) a display control unit configured to display the front image on a display unit before generation of the motion contrast image is completed.

20. The image processing apparatus according to claim 19, wherein the motion contrast image generating unit stops generating the motion contrast image on command from an examiner.

21. The image processing apparatus according to claim 19, wherein the display control unit displays a first front image which is the generated front image on the display unit before generation is completed of a second front image which is a different kind of image from the first front image and is the motion contrast image.

22. A system comprising: the image processing apparatus according to claim 19; and an optical coherence tomography apparatus including a detector arranged to detect an interference light obtained by coupling (a) a reference light and (b) a return light from the subject irradiated with the measuring light.

23. The image processing apparatus according to claim 19, wherein the motion contrast image generating unit generates the motion contrast image by using differences between temporally successive plural items of the plurality of items of three-dimensional tomographic data.

24. The image processing apparatus according to claim 19, wherein the plurality of units further comprises an analysis unit configured to analyze, by recognizing layer information, at least one item of three-dimensional tomographic data out of the plurality of items of three-dimensional tomographic data, and wherein the motion contrast image generating unit identifies tomographic data to be used to generate the motion contrast image, using the recognized layer information.

25. The image processing apparatus according to claim 24, wherein the motion contrast image generating unit identifies the tomographic data to be used to generate the motion contrast image, using the recognized layer information and an observation site set by an examiner.

26. The image processing apparatus according to claim 19, wherein the display control unit displays the front image or the motion contrast image on the display unit for determination of success or failure of acquiring of tomographic data to be used for generating the motion contrast image.

27. The image processing apparatus according to claim 19, wherein the display control unit displays, on the display unit, a button for reacquiring of tomographic data to be used for generating the motion contrast image.

28. An image processing apparatus that processes an image generated using at least one item of three-dimensional tomographic data out of a plurality of items of three-dimensional tomographic data obtained by conducting a plurality of optical coherence tomography scans of a subject at different times using measuring light controlled to scan a same position of the subject, the image processing apparatus comprising:
at least one of (a) at least one processor executing memory-stored instructions and (b) circuitry, configured to function as a plurality of units comprising:
(1) a motion contrast image generating unit configured to generate a plurality of motion contrast images of the subject using the plurality of items of three-dimensional tomographic data including three or more items of three-dimensional tomographic data and generate an averaged image of the plurality of motion contrast images; and
(2) a display control unit configured to display any of the plurality of motion contrast images on a display unit before the averaged image is displayed.

29. The imaging processing of claim 28, wherein:
each time a motion contrast is generated, the motion contrast image generating unit generates an averaged image of already generated motion contrast images in sequence; and
on the display unit, each time an averaged image is generated, the display control unit displays the averaged image in a display area for use to display averaged images by switching to the newly generated averaged image.

30. The image processing apparatus according to claim 28, wherein the motion contrast image generating unit stops generating the motion contrast image on command from an examiner.

31. A system comprising: the image processing apparatus according to claim 28; and an optical coherence tomography apparatus including a detector arranged to detect an interference light obtained by coupling (a) a reference light and (b) a return light from the subject irradiated with the measuring light.

32. The image processing apparatus according to claim 28, wherein the motion contrast image generating unit generates the motion contrast image by using differences between temporally successive plural items of the plurality of items of three-dimensional tomographic data.

33. The image processing apparatus according to claim 28, wherein the plurality of units further comprises an analysis unit configured to analyze, by recognizing layer information, at least one item of three-dimensional tomographic data out of the plurality of items of three-dimensional tomographic data, and wherein the motion contrast image generating unit identifies tomographic data to be used to generate the motion contrast image, using the recognized layer information.

34. The image processing apparatus according to claim 33, wherein the motion contrast image generating unit identifies the tomographic data to be used to generate the motion contrast image, using the recognized layer information and an observation site set by an examiner.

35. The image processing apparatus according to claim 28, wherein the display control unit displays the averaged image or any of the plurality of motion contrast images on the display unit for determination of success or failure of acquiring of tomographic data to be used for generating the motion contrast image.

36. The image processing apparatus according to claim 28, wherein the display control unit displays, on the display unit, a button for reacquiring of tomographic data to be used for generating the motion contrast image.

37. An image processing method for processing an image generated using at least one item of three-dimensional tomogrpahic data out of a plurality of items of three-dimensional tomogrpahic data obtained by conducting a plurality of optical cohenerence tomography scans of a subject at different times using measuring light controlled to scan a same position of the subject, the image processing method comprising:
generating a front image of the subject using the at least one item of three-dimensional tomographic data;
generating a motion contrast image of the subject using the plurality of items of three-dimensional tomographic data; and
displaying the front image on a display unit before displaying the motion contrast image.

38. A non-transitory computer-readable storage medium storing a program for causing a computer to execute the method according to claim 37.

39. An image processing method for processing an image generated using the at least one item of three-dimensional tomographic data out of a plurality of items of three-dimensional tomographic data obtained by the conducting a plurality of optical coherence tomography scans of a subject at different times using measuring light controlled to scan a same position of the subject, the image processing method comprising:
generating a front image of the subject using the at least one item of three-dimensional tomographic data;

generating a motion contrast image of the subject using the plurality of items of three-dimensional tomographic data; and displaying the front image on a display unit before generation of the motion contrast image is completed.

40. A non-transitory computer-readable storage medium storing a program for causing a computer to execute the method according to claim 39.

41. An image processing method for processing an image generated using at least one item of three-dimensional tomographic data out of a plurality of items of three-dimensional tomographic data obtained by conducting a plurality of optical coherence tomography scans of a subject at different times using light controlled to scan a same position of the subject, the image processing method comprising:

generating a plurality of motion contrast images of the subject using the plurality of items of three-dimensional tomographic data including three or more items of three-dimensional tomographic data and generating an averaged image of the plurality of motion contrast images; and displaying any of the plurality of motion contrast images on a display unit before the averaged image is displayed.

42. A non-transitory computer-readable storage medium storing a program for causing a computer to execute the method according to claim 41.

43. An image processing apparatus that processes an image generated using at least one item of tomographic data out of a plurality of items of tomographic data obtained by conducting a plurality of optical coherence tomography scans of a subject at different times using measuring light controlled to scan a same position of the subject, the image processing apparatus comprising:

at least one of (a) at least one processor executing memory-stored instructions and (b) circuitry, configured to function as a plurality of units comprising:

(1) a front image generating unit configured to generate a front image of the subject using the at least one item of tomographic data;

(2) a motion contrast image generating unit configured to generate a motion contrast image of the subject using the plurality of items of tomographic data; and (3) a display control unit configured to display, on a display unit, one image of the front image and the motion contrast image, and being capable of controlling display of an image to change display of the one image into display of the other image of the front image and the motion contrast image.

44. A system comprising: the image processing apparatus according to claim 43; and an optical coherence tomography apparatus including a detector arranged to detect an interference light obtained by coupling (a) a reference light and (b) a return light from the subject irradiated with the measuring light.

45. The image processing apparatus according to claim 43, wherein the motion contrast image generating unit generates the motion contrast image by using differences between temporally successive plural items of the plurality of items of tomographic data.

46. The image processing apparatus according to claim 43, wherein the plurality of units further comprises an analysis unit configured to analyze, by recognizing layer information, at least one item of tomographic data out of the plurality of items of tomographic data, and wherein the motion contrast image generating unit identifies tomographic data to be used to generate the motion contrast image, using the recognized layer information.

47. The image processing apparatus according to claim 46, wherein the motion contrast image generating unit identifies the tomographic data to be used to generate the motion contrast image, using the recognized layer information and an observation site set by an examiner.

48. The image processing apparatus according to claim 43, wherein the display control unit displays the front image or the motion contrast image on the display unit for determination of success or failure of acquiring of tomographic data to be used for generating the motion contrast image.

49. The image processing apparatus according to claim 43, wherein the display control unit displays, on the display unit, a button for reacquiring of tomographic data to be used for generating the motion contrast image.

50. An image processing method for processing an image generated using at least one item of tomographic data out of a plurality of items of tomographic data obtained by conducting a plurality of optical coherence tomography scans of a subject at different times using measuring light controlled to scan a same position of the subject, the image processing method comprising:

generating a front image of the subject using the at least one item of tomographic data;

generating a motion contrast image of the subject using the plurality of items of tomographic data; and displaying one image of the front image and the motion contrast image on a display unit, wherein display of an image is capable of being controlled to change display of the one image into display of the other image of the front image and the motion contrast image.

51. A non-transitory computer-readable storage medium storing a program for causing a computer to execute the method according to claim 50.

* * * * *